(12) United States Patent
Konya (10) Patent No.: US 8,795,594 B2
(45) Date of Patent: Aug. 5, 2014

(54) ANALYTICAL TEST APPARATUS COMPRISING A FRICTION CLUTCH

(75) Inventor: Ahmet Konya, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/359,220

(22) Filed: Jan. 26, 2012

(65) Prior Publication Data

US 2012/0122594 A1 May 17, 2012

Related U.S. Application Data

(63) Continuation of application No. PCT/EP2010/055906, filed on Apr. 30, 2010.

(30) Foreign Application Priority Data

Jul. 14, 2009 (EP) .................................... 09165425

(51) Int. Cl.
- *G01N 21/00* (2006.01)
- *B01L 3/00* (2006.01)
- *A61B 5/15* (2006.01)
- *F16D 7/02* (2006.01)
- *A61B 5/151* (2006.01)

(52) U.S. Cl.
CPC .............. F16D 7/025 (2013.01); A61B 5/1411 (2013.01); A61B 5/15146 (2013.01); F16D 7/028 (2013.01)
USPC .............................. 422/66; 422/410; 422/500

(58) Field of Classification Search
USPC ................ 422/410, 500; 464/43, 46
See application file for complete search history.

(56) References Cited

U.S. PATENT DOCUMENTS

| 3,092,983 A | 6/1963 | Huber |
| 4,043,149 A | 8/1977 | Tuninetti |

(Continued)

FOREIGN PATENT DOCUMENTS

| DE | 103 15 808 A1 | 10/2004 |
| DE | 20 2005 000 215 U1 | 6/2006 |

(Continued)

OTHER PUBLICATIONS

International Patent Application PCT/EP2010/055906 International Search Report mailed Jul. 6, 2010.

(Continued)

*Primary Examiner* — Dean Kwak
(74) *Attorney, Agent, or Firm* — Woodard, Emhardt, Moriarty, McNett & Henry LLP (57) ABSTRACT

An analytic test instrument (112) is proposed, which has at least one transport device (120) for an analysis tape (170), in particular a lancet tape. The analysis tape (170) comprises a plurality of analytic aids (172) that can be used in succession. The transport device (120) comprises at least one friction clutch (110). The friction clutch (110) has at least one first friction element (148) that can be coupled to a drive (186) and at least one second friction element (150) that can be coupled to the analysis tape (170), in particular a reel (118) of the analysis tape (170). The first friction element (148) and the second friction element (150) are coupled by friction such that the first friction element (148) entrains the second friction element (150) in a first torque range and slips over the second friction element (150) in a second torque range.

12 Claims, 4 Drawing Sheets

(56) References Cited

U.S. PATENT DOCUMENTS

| | | | | |
|---|---|---|---|---|
| 2005/0090850 | A1* | 4/2005 | Thoes et al. | 606/182 |
| 2006/0002816 | A1* | 1/2006 | Zimmer et al. | 422/56 |
| 2010/0216246 | A1* | 8/2010 | Konya et al. | 436/43 |

FOREIGN PATENT DOCUMENTS

| | | |
|---|---|---|
| EP | 0 905 400 A2 | 3/1999 |
| FR | 2 353 753 | 12/1977 |
| GB | 2 321 504 A | 7/1998 |
| GB | 2 404 703 A | 2/2005 |
| WO | WO 2008/138443 A1 | 11/2008 |
| WO | WO 2009/037341 A1 | 3/2009 |
| WO | WO 2009037341 A1 * | 3/2009 |

OTHER PUBLICATIONS

International Patent Application PCT/EP2010/055906 English Translation of International Preliminary Report on Patentability mailed Jan. 18, 2012.

* cited by examiner

ANALYTICAL TEST APPARATUS COMPRISING A FRICTION CLUTCH

CROSS-REFERENCE TO RELATED APPLICATION

This application is a continuation of International Application No. PCT/EP2010/055906 filed Apr. 30, 2010, which claims the benefit of European Application No. 09165425.1, filed Jul. 14, 2009, the entire disclosures of which are hereby incorporated by reference.

FIELD

The invention relates to an analytic test instrument with at least one friction clutch and to a tape magazine for use in such an analytic test instrument. Such analytic test instruments and tape magazines are used in particular in the field of medical diagnostics, particularly within the scope of detecting at least one analyte in a bodily fluid. In particular, this analyte may be glucose, for example blood glucose and/or glucose in interstitial fluid. However, in principle, other fields of application are also possible.

BACKGROUND

Medical diagnostics, but also other fields, encounter the problem of needing to detect specific analytes quickly and reliably, sometimes even a number times in a day. By way of example, diabetics often have to monitor their blood glucose levels up to seven times a day. So as not to restrict the daily routine of the user more than necessary as a result of these frequent checks, hand-held instruments were developed that also allow monitoring the blood glucose levels during free time or at work. Here, a lancet punctures skin of the user, for example on a finger tip or on an ear lobe. This generates a blood sample or a sample of interstitial fluid. This sample is then examined in respect of its blood sugar level and/or the level of another type of analyte by means of a test instrument and a test element, for example an electrochemical and/or optical test element.

In addition to individual strip test instruments, tape instruments have also been disclosed in the meantime; here, test elements are provided in the form of test tapes. These test tapes contain a plurality of test fields with corresponding test chemicals, the properties of which change in the case of contact with the analyte to be detected. In addition to analytic test instruments with analysis tapes in the form of test tapes, analytic test instruments with analysis tapes that contain a plurality of lancets have also been disclosed in the meantime. Here, lancets are successively provided on a carrier tape in an application position of the test instrument and can be used for generating the sample. By way of example, the analysis tape can be provided by a supply reel, with used analytic aid, e.g. test fields and/or lancet elements, are wound up on a take-up reel after use.

WO 2008/138443 A1 shows a pricking system with a carrier tape that carries a plurality of lancets. Furthermore, provision is made for a conveyor apparatus for successively bringing the lancets into an application position by moving the carrier band in a conveying direction. Moreover, provision is made for an actuation device for driving the conveyor apparatus. The pricking system furthermore comprises a detachable lock that blocks further transport of the carrier tape as soon as a lancet has reached the usage position.

WO 2009/037341 A1 has disclosed a sample extraction system for extracting a liquid sample, which system has at least one analytic aid. The sample extraction system has a coupling element for coupling onto the analytic aid and at least one drive unit for driving a movement of the coupling element from a rest position into an extended position. The drive unit comprises an energy transducer that is embodied to produce a rotational movement with different directions of rotation. The drive unit furthermore has a coupling device with at least one rotational direction-sensitive element that is designed to couple the energy transducer to a first system function in the case of a first rotational direction and to couple said energy transducer to a second system function that differs from the first system function in the case of a second rotational direction that differs from the first rotational direction.

For different reasons, both WO 2008/138443 A1 and WO 2009/037341 A1 disclose so-called friction clutches in various embodiments, particularly in a drive for the analysis tapes. By way of example, these friction couplings can comprise spiral-spring elements. Here, all the friction clutches disclosed in these documents are based on the fact that one or more resilient, elastic or spring-mounted arms or other types of elastic pick-up elements such as spiral springs slip in a punctiform fashion on a friction surface of a counterelement and interact with projections on this counterelement. The pick-up elements catch on these projections and entrain these as long as a maximum torque is not exceeded. This maximum torque is specified by the elasticity and shape of the pick-up elements and projections because as the torque increases the pick-up elements are pressed away from the friction surface of the counterelement and/or the projections and slip over these projections above the maximum torque. However, this means that the maximum torque or limit torque is fixedly prescribed by the geometry of the projections and the pick-up elements, and by the material properties and bending moments of the pick-up elements, and, in particular, cannot be adjusted. Furthermore, significant amounts of noise are generated when the pick-up elements slip over the projections. Such spring-based friction clutches are often also referred to as free wheels or are embodied as free wheels.

By way of example, the pricking system configuration with the conveyor apparatus disclosed in WO 2009/037341 A1 generally requires at least one friction clutch for three reasons. Thus, a friction clutch may be provided to compensate for tolerances that emerge from the production of the analysis tapes. Furthermore, the friction clutch is provided to compensate for the variation in the take-up reel diameter, which increases during continued cycling. Thirdly, the friction clutch is designed to prevent mechanical damage to the tape because, once the lancet has reached the usage position, unintentional further transport could lead to the lancet becoming detached or the analysis tape becoming deformed. The friction clutch ensures that the drive is released by slipping through before there is such mechanical damage to the tape, and so mechanical overstress is avoided. By way of example, spiral springs can be used for this.

There is a change in the roll thickness on both a supply reel and a take-up reel as a result of e.g. winding up the tape, particularly when conveying lancet tapes but also in the case of other types of analysis tapes, and so different travel paths of the tape have to be overcome whilst applying the same force per continued cycle. If the travel path of the roll is very short, the excessive force must be dissipated. By way of example, this is achieved by the friction clutch. Here, provision can for example be made for metal springs that are constantly under a certain amount of pressure, resulting in constant tensile force acting on the tape.

However, the systems known from the prior art have various disadvantages or technical challenges, particularly for the use of lancet tapes. Thus, for example, as set out above, WO 2008/138443 A1 provides a detachable lock, for example in the form of a gripper, that both serves to stop the tape if the lancet is transported past it and also is used for the pricking procedure. However, in the friction clutches known from the prior art, a permanent force acts on the analysis tape, for example as a result of the pretensioned spiral springs. These spiral springs, e.g. metal springs, are always under a specific pressure, as a result of which a constant tensile force acts on the tape. As a result, the user must also apply more force to operate the system, which may be disadvantageous; this is the case in e.g. the system described in WO 2008/138443 A1. A further disadvantage relates to the acoustic component since minimum dead travel must be implemented; this can generate uncomfortable background noise. This is based on the functionality of a spring friction clutch, which contracts and slips over obstacles. Noise is generated every time an obstacle is overcome. However, in order to achieve as little dead travel as possible, a plurality of these obstacles are required, distributed over 360°. A further disadvantage consists of the fact that a difficulty in known spiral-spring systems lies in providing springs whose physical volume can be accommodated in the core of a reel; this may, in certain circumstances, lead to an increase in the overall size of the system as a result of this component.

Hence, in conclusion, known spring friction clutches for test instruments are disadvantageous in having a dead travel, which in many cases does not allow precise gripping of the friction clutch. Furthermore, significant amounts of noise are generated as a result of the punctiform interaction between the pick-up elements and projections; this noise can in particular lead to the user experiencing insecurity and can significantly reduce user comfort. Furthermore, the maximum torques of the friction clutches are generally fixedly prescribed by geometries and material properties of the pick-up elements and/or projections and cannot be adjusted.

In principle, friction clutches are known from heavy mechanical engineering. Thus, for example, DE 10315808 A1 describes a friction clutch with a sleeve-shaped hub for holding a drive element and a clamping part, situated at the end, with a slit extending in the region of a radial central plane and with a clamping screw bridging the slit and acting in the circumferential direction of the clamping part. A drive element is arranged between two friction linings, which are in turn arranged axially between a pressure disk and the clamping part and are acted upon in an adjustable fashion via an adjusting nut by means of a spring force. The clamping part and the sleeve-shaped hub have an integral design.

GB 2321504 A describes a friction clutch with a first ring and two internal rings, which each have frustoconical coupling surfaces that engage in one another. The magnitude of the generated frictional force, which is exerted perpendicular to the coupling surfaces, is varied by means of an adjustment member.

However, the last-mentioned friction clutches known from the prior art have previously only been known in the field of heavy mechanical engineering. Thus, for example, the one in DE 103 15 808 A1 is used to drive chain wheels. Accordingly, the known friction clutches are generally comparatively heavy, composed of many parts and have a high installation space. Until now there has not been a demand to use such friction clutches in the field of medical technology, particularly in the field of analytic test instruments.

SUMMARY

It is therefore an object of the invention to specify an analytic test instrument and a tape magazine for use in such an analytic test instrument, which at least largely avoid the disadvantages from the prior art. In particular, transporting the analysis tape with as little noise as possible should be ensured, without having to apply an additional force as a result of pretensioning; this should require as little installation space as possible and moreover be cost-effective.

This object is achieved by an analytic test instrument, a tape magazine and use with the features of the independent claims. Advantageous developments of the inventions, which can be implemented individually or in combination, are illustrated in the dependent claims.

An analytic test instrument is proposed in a first aspect of the invention. In general terms, an analytic test instrument should be understood to mean a device that can be used within the scope of an analysis, for example for detecting one or more analytes in a bodily fluid. Accordingly, the analytic test instrument can have a sample-taking function for generating one or more samples and/or an analysis function. In the following text, reference is substantially made to analytic test instruments that only have a sample-taking function in the form of a lancet function. However, use can alternatively or additionally also be made of other types of analytic test instruments. The analytic test instrument can in particular be embodied as a hand-held instrument.

The analytic test instrument is based on the use of at least one analysis tape, which is wholly or partly held in the analytic test instrument. By way of example, this analysis tape can be part of a tape magazine, for example a tape magazine according to the invention as per a further aspect of the invention, explained in more detail below.

In principle, an analysis tape should in this case be understood to mean any tape that can be used within the scope of an analysis, for example within the scope of detecting one or more analytes in a bodily fluid. Accordingly, the analysis tape can for example have a plurality of analytic aids, for example a plurality of test fields and/or a plurality of lancets. The plurality of analytic aids can be used successively in the analytic test instrument. By way of example, the test fields can have test chemicals, which change at least one measurable property, for example a physically and/or chemically measurable property, in the presence of the at least one analyte to be detected. Without restricting further possible embodiments, reference is made below to lancet tapes in particular, i.e. to analysis tapes that only comprise lancets as analytic aid. However, other embodiments are also possible, for example embodiments in which the analysis tape has both lancets and test fields.

The analytic test instrument can use the transport device to bring, for example successively, the analytic aids into at least one application position. Here, the transport device comprises at least one friction clutch. Here, in principle, a friction clutch should be understood to mean any clutch that has a safety function in the form of an independently torque-switching shift.

In contrast to the prior art cited above, an idea of the invention is based on using a friction clutch that is based on friction. Accordingly, the friction clutch can, according to the invention, be embodied such that it has an entraining effect until it overcomes a torque that corresponds to the static friction, whereas there is no longer an entraining effect above a torque range in which the static friction has been overcome and it is merely dynamic friction that still acts. As a result, the proposed friction clutch is different to the friction clutches known from WO 2009/037341 A1 or WO 2008/138443 A1, which are based on punctiform interaction between pick-up elements and projections.

Accordingly, it is proposed that the friction clutch has at least one first friction element that can be coupled, in particular is coupled, to a drive and at least one second friction element that can be coupled, in particular is coupled, to the analysis tape, in particular a reel of the analysis tape. The first friction element and the second friction element are coupled to one another by friction such that the first friction element entrains the second friction element, i.e. transmits torque thereto, in a first torque range and slips over the second friction element, i.e. transmits no or very little torque thereto, in a second torque range, in particular in a torque range that is greater than the first torque range. In principle, the friction coupling between the first friction element and the second friction element can be direct or indirect in this case, with direct friction coupling involving direct contact between corresponding friction surfaces of the first and second friction element, whereas indirect friction coupling involves indirect contact via at least one intermediate element. Accordingly, the first friction element can also directly or indirectly slip over the second friction element in the second torque range, with indirect slipping involving slipping over at least one intermediate element.

In general, a district boundary may be prescribed between the first torque range and the second torque range, or else there may be a continuous transition region. The boundary is generally, as set out above, prescribed by a transition from static friction to dynamic friction, i.e., for example, by a point at which the first friction element "breaks free" from the second friction element, or vice versa. As a result of this the proposed friction clutch is also different from the friction clutches known from WO 2009/037341 A1 or WO 2008/138443 A1, in which there is no coupling by friction but an interlocking interaction between a pick-up element and at least one projection. In the proposed friction clutch, a maximum torque or limit torque, i.e. the transition between the first torque range and the second torque range, is preferably given by the transition between static friction and dynamic friction between the first friction element and the second friction element, in particular only as result of this transition between static friction and dynamic friction, preferably without additional influencing factors such as e.g. bending moments or spring forces.

Here, friction coupling should be understood to mean an interaction between two elements (the first friction element and the second friction element in the present case), in which entrainment is the result of frictional forces, preferably as the result of only frictional forces. In particular, entrainment can be brought about by virtue of the fact that the first friction element and the second friction element lie on one another on at least locally parallel friction surfaces. The frictional forces can then act in the plane of the parallel friction surfaces. Mechanical pick-up elements, on which pressure and/or tensile forces are directly applied, are preferably not provided.

The friction coupling between the friction elements is preferably continuous over the entire angular range of the friction clutch, i.e. for example over 360°. This means that the friction elements lie on one another over the entire rotational angle range of the friction clutch, contrary to e.g. the friction clutches known from WO 2009/037341 A1 or WO 2008/138443 A1. Here, the friction surfaces can preferably be embodied as closed friction surfaces, which have a continuous design over the whole angular range. However, alternatively, one or more of the friction surfaces, rubbing against one another, of the friction elements can also have a discontinuous design. Continuous friction coupling over the entire rotational angle range prevents the occurrence of dead travel. Furthermore, this can prevent noise from being generated. In particular, it is possible, within the scope of the present invention, to implement a continuous increase in the torque over the entire angular range within which the friction elements can be rotated with respect to one another, in contrast to the discontinuous design as per the friction clutches described in WO 2009/037341 A1 or WO 2008/138443 A1, in which torque is merely overcome at the projections.

The use of friction coupling in place of an interlocking interaction between bendable pick-up elements and one or more projections and the application of local tensile forces connected with this, as in e.g. WO 2009/037341 A1 or WO 2008/138443 A1, furthermore offers the advantage of being able to set very precisely the maximum torque above which the breaking free occurs. Thus, the friction coupling is generally defined by contact forces by means of which the friction elements are pressed against one another. However, these contact forces can be prescribed very precisely or can even be adjusted. The first friction element and the second friction element have an unchanging shape, preferably in the region of their interacting friction surfaces, over the entire torque range and/or angular range, in contrast to e.g. WO 2009/037341 A1 or WO 2008/138443 A1.

The friction clutch can, in particular, be arranged between a driven axle and an element surrounding the axle, in particular a reel of the analysis tape (e.g. a supply reel and/or a take-up reel).

The friction elements can be made both of the same material and of different materials. All that is preferred is the presence of an adjustable boundary of the transition between static friction and dynamic friction. The at least one first friction element and the at least one second friction element can rub directly against one another and hence themselves provide the friction surfaces between which there is friction coupling. However, alternatively, or in addition thereto, provision can for example also be made for one or more intermediate elements, e.g. the O-ring described in more detail below, between the first friction element and the second friction element, as will be described in more detail below. Hence, the friction coupling between the first friction element and the second friction element can be brought about via at least one intermediate element, in particular at least one O-ring. The advantage of this embodiment variant lies in the possibility of saving installation space because, for example, the O-ring can apply the pretension force of the friction clutch. The O-ring can then act like a spring element, and so no separate spring element is required.

As illustrated above, the friction clutch can in particular be arranged between a driven axle and an element surrounding the axle in particular a reel of the analysis tape. By way of example, the friction clutch can partly or wholly be surrounded by the reel. By way of example, this driven axle can be embodied as part of the transport device and/or as part of a tape magazine. The drive can for example be brought about via at least one drive belt and/or via at least one gearwheel. The reel of the analysis tape can in particular be a supply reel and/or a take-up reel of the analysis tape. However, in general it is the take-up reel that is driven.

In this embodiment (however, in principle this also holds true for other embodiments), it is particularly preferred if the second friction element is embedded between at least two first friction elements in the axial direction, for example, by firstly arranging in the axial direction, i.e. parallel to the axle, at least one example of a first friction element, then at least one second friction element and subsequently a second example of a first friction element, which may have the same or a different embodiment to the first example. A sequence with more than two transitions between a first and a second friction element is also possible. In particular, the friction surfaces can be oriented perpendicular to the axle. At least one axial force component preferably acts on the second friction element. Here, as will become clearer from the following exemplary embodiments, the force acting on the second friction element can act purely in the axial direction; however, it can also have components in a radial direction. However, a reverse embodiment is also possible, i.e. an embodiment in which at least one first friction element is embedded between two or more second friction elements. Furthermore, embedding in the radial direction is also feasible.

The first friction element and/or the second friction element can comprise at least one friction sleeve, in particular at least one axially aligned friction sleeve. Here, a friction sleeve should in principle be understood to mean an element with any shape, for example a sleeve-shaped element, that provides at least one friction surface. Here, an axial alignment should be understood to mean an alignment in which there is entrainment as a result of an axial frictional force, i.e. a frictional force that is aligned substantially parallel to the axle, i.e. with an angle of at most 20° from the axle, preferably at most 10°, and particularly preferably at most 5°. However, the axial alignment does not preclude tangential entrainment of the take-up reel. In principle, another embodiment is also possible.

The friction sleeve can for example be inserted between the analysis tape and the drive, for example between a take-up reel and a body of the friction clutch. The friction sleeve can for example be embodied as cylinder ring or cylinder sleeve. The friction sleeve can for example be connected to the take-up reel or be formed integrally with the take-up reel. Alternatively, or in addition thereto, the friction sleeve can also be formed integrally with the body of the friction clutch, or be connected to the latter. The friction sleeve can preferably also be mounted in a moveable fashion in an axial direction, for example moveably on a body of the friction clutch. The friction sleeve can have an integral or else a multipart design. By way of example, the friction sleeve can be connected to the axle and/or a body of the friction clutch and/or the reel, for example the take-up reel, by means of one or more pick-up pins.

The proposed embodiment, particularly when using one or more friction sleeves, allows a particularly installation space-saving production of a friction clutch. In particular, compared to friction coupled friction clutches known from the prior art, the number of parts can be significantly reduced.

In one embodiment of the invention, the first friction element and/or the second friction element can in particular comprise at least one conical friction surface. Here, it is particularly expedient if the friction sleeve (should such a friction sleeve be provided) comprises at least one friction surface that is tilted with respect to the axle, wherein the first friction element comprises at least one conical friction surface arranged in a concentric fashion to the axle, which conical friction surfaces interacts, coupled by friction, with the tilted friction surface. As a result, this can for example let the conical friction surface have an axially encircling embodiment, whereas the friction sleeve lies on this conical friction surface at points, over a relatively large angular range or likewise in a completely encircling fashion, and brings about the aforementioned friction coupling.

Here, the conical friction surface may also have a multipart design. By way of example, the conical friction surface can comprise a first conical surface arranged on a first side of the friction sleeve and a second conical surface arranged on an opposite side of the friction sleeve.

Here, the conical friction surfaces and/or friction sleeves can also have an interlocking design in a sectional plane perpendicular to the axle. Thus, for example, arranged in a sectional plane perpendicular to the axle and starting from the axle, there may firstly be at least one second friction sleeve associated with the reel and having at least one outwardly pointing friction surface, followed by at least one first friction sleeve associated with the axle or a body of the friction clutch and having at least one first friction surface, which points to the axle and interacts with the second friction surface. Then the first friction surface can for example be embodied such that it encloses the second friction surface at least in sections, and preferably entirely. Thus, the friction surfaces can engage in or interlock with one another, which further increases the stability of the friction clutch.

If use is made of an embodiment with the conical surface, contact forces between the first friction element and the second friction element do not only act in the axial direction, but also in a radial direction. Additionally, embodiments are also possible in which only axial contact forces act. Thus, for example, an axially directed force can be applied to a first side of the friction sleeve and a counterforce, likewise only in the axial direction, can be applied to a second side. In general, embodiments are feasible in which only axial forces, only radial forces or forces with components in both the axial and radial directions are implemented. The described embodiment with the at least one conical friction surface is an exemplary embodiment of the last variant.

As described above, one or more intermediate elements, which bring about the friction coupling, can be provided between the first friction element and the second friction element. In this case the first friction element does not lie directly on the second friction element but rather there is a division of the friction coupling into a number of material pairings, namely at least one material pairing of the at least one first friction element with the at least one intermediate element and at least one material pairing of the at least one intermediate element with the at least one second friction element. The at least one intermediate element, for example the at least one O-ring, can also exert or develop a spring effect, and so, for example, pretension is implemented between the first friction element and the second friction element. By way of example, the at least one intermediate element, more particularly the at least one O-ring, can have at least partly elastic properties and/or have an at least elastically deformable design. The intermediate element can also at least in part co-assume the function of a spring element, and so an additional optional spring element can be saved. However, alternatively, or in addition thereto, provision can optionally be made for a spring element, for example a metal spring. Exemplary embodiments will be explained in more detail below.

The intermediate element can in particular comprise at least one O-ring, or can be embodied as an O-ring. Accordingly, the friction coupling between the first friction element and the second friction element can for example be brought about via at least one O-ring. Here, an O-ring should be understood to mean a preferably flexible, closed annular element, which can for example have a round or polygonal cross section. By way of example, the O-ring can be produced from a plastics material, for example an elastomer or a thermoplastic. By way of example, the O-ring can wholly or partly be produced from a caoutchouc material or else a flouroelastomer, e.g. from Viton. Other materials are also possible.

The friction coupling between the first friction element and the second friction element can preferably be designed such that it is adjustable. Thus, for example, at least one adjustment element can be provided, by means of which it is possible to adjust a frictional force between the first friction element and the second friction element. By way of example, this can adjust the transition between the static friction and the dynamic friction, which preferably defines the switching point of the friction clutch. By way of example, this adjustment can set a delivery state of the analytic test instrument. However, an adjustment by a user of the analytic test instrument is preferably not an option. By way of example, the adjustment element can for example comprise at least one adjustment nut. However, alternatively, or in addition thereto, other embodiments of the adjustment element are, in principle, also possible. Furthermore, as an alternative to the adjustment element, or in addition thereto, provision can be made for at least one spring element that is designed to influence a frictional force between the first friction element and the second friction element. By way of example, the spring element can be designed to press the first friction element onto the second friction element, or vice versa. This can in particular ensure a constant frictional force or constant force conditions, and the friction clutch can be designed in a mechanically more robust fashion.

The option of an adjustable implementation of the friction coupling and, in particular, of the maximum torque is a decisive advantage of the proposed friction clutch over, for example, WO 2009/037341 A1 or WO 2008/138443 A1. However, alternatively, the friction coupling can also be embodied provided with a fixed specification. By way of example, the friction coupling can be determined once in a suitable fashion and a fixed fixing can then be derived therefrom, for example by a relative alignment of individual components with subsequent fixing. The latter can for example be brought about by a snap-on closure, a shaft seal or similar fixing elements. Alternatively, or in addition thereto, use can be made of bonding connection techniques for fixing, for example adhesive bonding and/or welding.

As described above, the analysis tape can for example be introduced into the analytic test instrument by means of one or more reels. This insertion can also take place in a replaceable fashion, in particular with the aid of a tape magazine, which can be held in a basic instrument of the analytic test instrument. Here, the transport device can be distributed over the basic instrument and the tape magazine. Accordingly, the friction clutch can wholly or partly be part of the basic instrument, or else it can wholly or partly be part of the tape magazine, for example part of a reel of the tape magazine. Thus, the at least one friction clutch can for example be contained in the basic instrument, in the tape magazine, or distributed over the basic instrument and the tape magazine. Provision can also be made for a plurality of friction clutches, which can be distributed over the basic instrument and the tape magazine.

In accordance with these options, a further aspect of the invention proposes a tape magazine for use in an analytic test instrument as per one or more of the above-described embodiments. The tape magazine comprises at least one analysis tape, wherein reference can be made to the above description. Moreover, the tape magazine can for example comprise a supply reel or a take-up reel. The friction clutch can in this case wholly or partly be contained within the tape magazine. In respect of the possible embodiments of the friction clutch, reference may in this case be made to the above description.

In a further aspect of the present invention, the use of a friction clutch in a transport device for an analysis tape in an analytic test instrument is proposed in general terms. The analytic test instrument may in particular be an analytic test instrument as per one or more of the above-described embodiments, and so reference can be made to the above description in respect of possible embodiments of the analytic test instrument. The analysis tape has a plurality of analytic aids, e.g. lancets and/or test fields, that can be used in succession. The friction clutch has at least one first friction element that can be coupled, in particular is coupled, to a drive of the transport device and at least one second friction element that can be coupled, in particular is coupled, to the analysis tape, in particular a reel of the analysis tape (e.g. a supply reel and/or a take-up reel). The first friction element and the second friction element are coupled by friction to one another such that the first friction element entrains the second friction element in a first torque range and slips over the second friction element in a second torque range. Reference can be made to the above description in respect of further possible embodiments.

The analytic test instrument, the tape magazine and the use have numerous advantages over the prior art. Thus, in particular, the object defined above can be implemented, and a transport device that is free from noise can be implemented. In principle, this requires no additional force to be applied, for example as a result of pretensioning a spring. Moreover, the friction clutch can be implemented so as to occupy minimal installation space and thus be easily integrated into the transport device. The friction clutch can moreover be produced in a cost-effective fashion. The proposed concept can be adjusted so as to be capable of production in series, for example by means of the above-described adjustment element. Furthermore, it is possible to prevent force from being exerted onto the analysis tape in a rest state.

BRIEF DESCRIPTION OF THE DRAWINGS

Further details and features of the invention emerge from the subsequent description of preferred exemplary embodiments, particularly in conjunction with the dependent claims. Here, the respective features can be implemented individually or together in combination with one another. The invention is not restricted to the exemplary embodiments. The exemplary embodiments are illustrated schematically in the figures. Here, the same reference signs in the individual figures denote equivalent or functionally equivalent elements, or elements with corresponding functions.

In detail.

DETAILED DESCRIPTION

Figure 1:
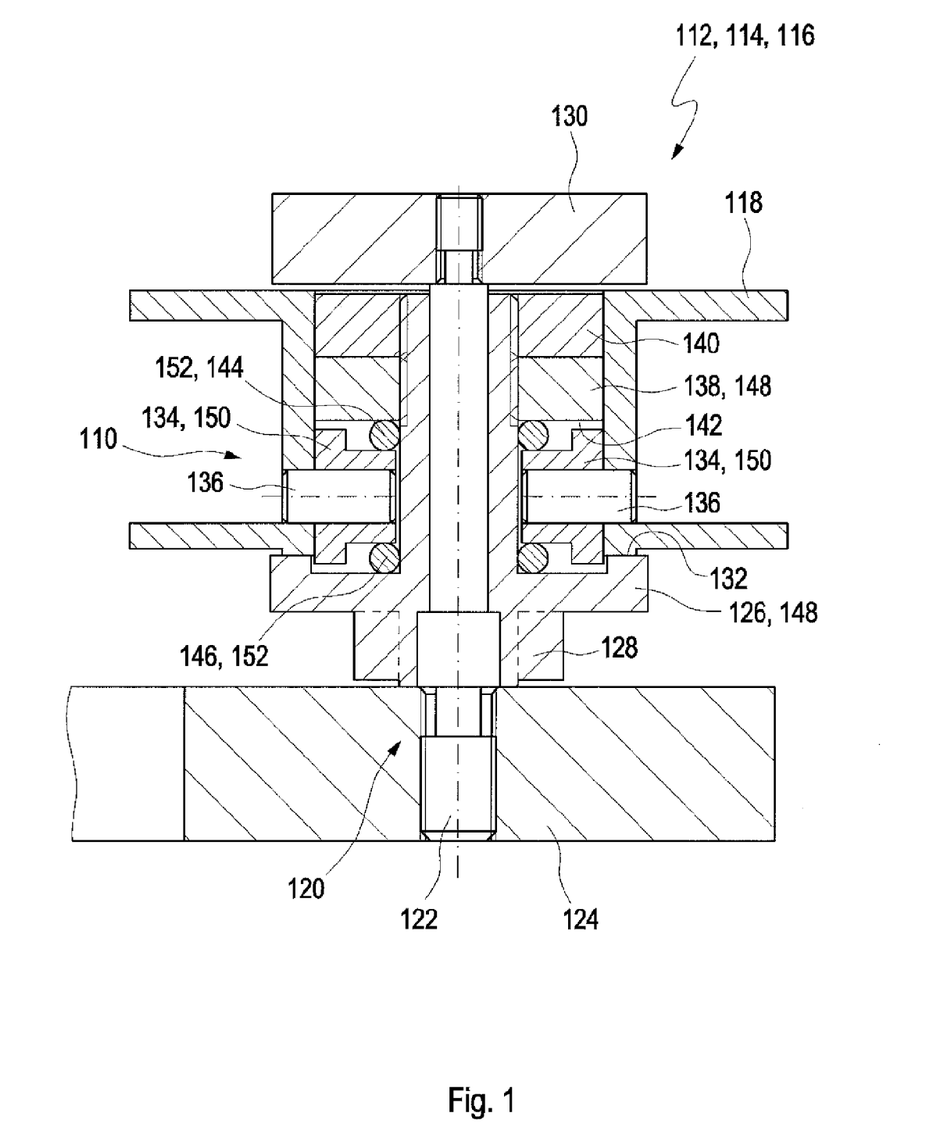
FIG. 1 shows a sectional view of a first exemplary embodiment of a friction clutch for an analytic test instrument.

FIG. 1 shows a sectional illustration of a first exemplary embodiment of a friction clutch 110 from the side. This friction clutch 110 can be used in an analytic test instrument 112, the latter merely being shown in sections in FIG. 1. By way of example, the friction clutch 110 may wholly or partly be a component of a tape magazine 114 and/or a basic instrument 116 of the analytic test instrument, which interacts with the tape magazine 114. However, in principle, other embodiments are also possible. In respect of examples of other embodiments of the analytic test instrument 112, reference can be made to WO 2008/138443 A1 and WO 2009/037341 A1. The test instruments illustrated therein can in principle also be modified within the scope of the present invention by using the illustrated friction clutch 110. However, in principle, use can also be made of other analytic test instruments 112, for example a simple exemplary embodiment of an analytic test instrument 112 illustrated in FIG. 3.

In the illustrated exemplary embodiment, the analytic test instrument 112 comprises a take-up reel 118, onto which used sections of an analysis tape, e.g. a lancet tape, are wound. The analysis tape has not been illustrated in FIG. 1.

Furthermore, the analytic test instrument 112 comprises a transport device 120, partly illustrated in FIG. 1, for transporting the analysis tape, more particularly for continued cycling of respectively one analytic aid, for example a lancet, into an application position. The transport device 120 comprises an axle 122, which can for example be mounted in a basic instrument. In the illustrated exemplary embodiment, this axle 122 is mounted in a basic plate 124.

In the illustrated exemplary embodiment, a gearwheel axle 126 is optionally applied to, e.g. plugged onto, this axle 122. Here the gearwheel axle 126 has a sleeve-like design and for example has a gearwheel 128 on its lower end, which gearwheel can for example be driven by means of an appropriate drive mechanism. However, in principle, a different type of drive is also possible. At its upper end, the gearwheel axle 126 is secured by a securing nut 130, which can for example be plugged and/or screwed onto the axle 122.

Thus, a two-part embodiment of an axle structure is provided in the illustrated exemplary embodiment, namely in the form of an axle 122 and a separate gearwheel axle 126. However, in principle, an integral design would also be feasible, in which the axle 122 and the gearwheel axle 126 are combined in one component.

In the illustrated exemplary embodiment, the gearwheel axle 126 optionally has a step 132. This step 132 holds the take-up reel 118, and so the latter concentrically surrounds the gearwheel axle 126 above the step 132. In the illustrated exemplary embodiment, the take-up reel 118 has two friction sleeves 134 situated diametrically opposite one another, for example friction sleeves 134 made of a plastics material. These are connected to the take-up reel 118, or a basic body of the take-up reel 118, via pick-up pins 136. However, in principle, an integral embodiment of the friction sleeves 134 with the basic body of the take-up reel 118 would also be possible. A number of friction sleeves 134 that differs from two would also be feasible, for example an embodiment with more than two friction sleeves 134 and/or an embodiment with a single friction sleeve 134, for example a friction sleeve encircling over a larger angle, up to 360°.

In the illustrated exemplary embodiment, the friction sleeves 134 are embedded in the axial direction between the step 134 of the gearwheel axle 126 and an adjustment nut 138. The adjustment nut 138 can in turn be secured at its upper end by a lock nut 140. The adjustment nut 138 and the lock nut 140 can for example be screwed onto a male thread of the gearwheel axle 126.

A first O-ring 144 is provided in the illustrated exemplary embodiment between an underside 142 of the adjustment nut 138 and the friction sleeves 134. In a similar fashion, a second O-ring 146 is provided between the friction sleeves 134 and the step 132. Here, the friction sleeves 134 are embodied such that these do not form further friction surfaces with the gearwheel axle 126. The gearwheel axle 126 and the adjustment nut 138, which can also be considered part of the gearwheel axle 126, therefore form a first friction element 148, and the friction sleeve 134 forms a second friction element 150. Friction coupling is brought about between these friction elements 148, 150, which friction coupling, in a low torque range in which static friction has not yet been overcome between these friction elements 148, 150, brings about fiction coupling and hence an entrainment effect, whereas there no longer is an entrainment effect once the static friction has been overcome and there is an onset of dynamic friction. Above this limit torque the first friction element 148 slips over the second friction element 150 without an entrainment effect. Here, in the illustrated exemplary embodiment, the friction coupling is brought about by intermediate elements 152 in the form of the O-rings 144, 146. However, in principle, direct friction coupling would also be possible.

In this first illustrated variant of the friction clutch 110, the torque is thus transmitted onto the take-up reel 118 by means of the O-rings 144, 146. By way of example, it may be that merely a contact force, which presses the first friction element 148 onto the second friction element 150 or vice versa, acts in the axial direction. This contact force can be adjusted by means of the adjustment nut 138. During torque transmission, the gearwheel 128 on the gearwheel axle 126 is rotated, as a result of which the gearwheel axle 126 is rotated and acts on the O-rings 144, 146 as a result of friction coupling. These O-rings are preferably arranged such that no further friction surface has an influence on the torque to be transmitted. The adjustment nut 138 is used to set the pretension of the O-rings between the gearwheel or gearwheel axle 126 and the friction sleeves 134, which entrain the take-up reel 118. To this end, use is preferably made of a fine thread in order to allow an adjustment that is as fine as possible. However, in series production, use can in principle also be made of another type of connection in place of such a fine adjustment using a fine thread, for example, taking account of the tolerances, use can be made of a fixed snap-on connection or a similar connection, which could significantly reduce assembly and adjustment complexity. The costs associated with this could also be reduced thereby.

Figure 2:
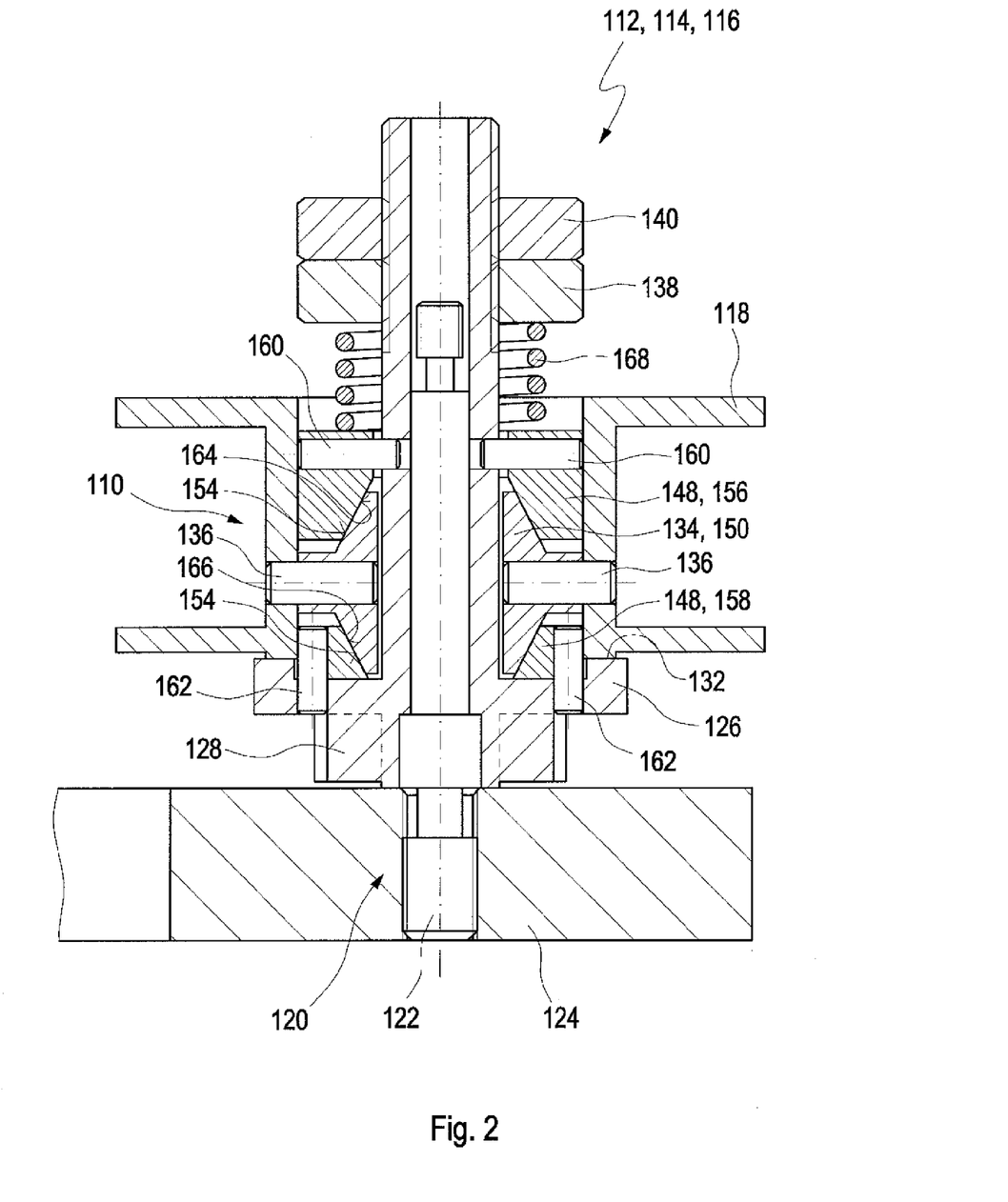
FIG. 2 shows a second exemplary embodiment of a friction clutch for an analytic test instrument.

Like the exemplary embodiment illustrated in FIG. 2 as well, the illustrated exemplary embodiment of the friction clutch 110 can also, in principle, be modified within the scope of the invention. Thus, for example, another element could also be driven instead of a take-up reel 118, for example a supply reel; however, this is less preferable.

By way of example, the illustrated components can wholly or partly be produced from metallic and/or plastics components. In the process, as explained above, an embodiment can for example be selected in which the same material pairings are present at each contact point between the friction elements 148, 150. Thus, for example, the adjustment nut 138 and the gearwheel axle 126 or the step 132 could be produced from identical materials such that the same material pairings occur at each friction point, for example a first material pairing at all boundary surfaces between the adjustment nut or the step 132, and the O-rings 144, 146 and a second material pairing at all boundary surfaces between the O-rings 144, 146 and the friction sleeves 134. However, in principle, another embodiment is also possible, i.e. an embodiment with different materials or different material pairings.

Furthermore, reference is once again made to the fact that the friction clutch 110 can also wholly or partly be integrated into the reel, for example the take-up reel 118. Accordingly, the friction clutch can ideally also e.g. wholly or partly be a component of a tape magazine 114, which can be held in a replaceable fashion in a basic instrument 116 in the analytic test instrument 112.

FIG. 2 shows, in an illustration analogous to FIG. 1, a second exemplary embodiment of a friction clutch 110. The latter is in turn held in an analytic test instrument 112, for example wholly or partly in a tape magazine 114, for example in a take-up reel 118 of a tape magazine 114. In respect of exemplary embodiments of possible analytic test instruments 112 in which the friction clutch 110 as per FIG. 2 may be used, reference can in turn be made to e.g. WO 2008/138443 A1 or WO 2009/037341 A1, or to the analytic test instrument 112 as per FIG. 3. However, in principle, other embodiments are also possible.

The analytic test instrument 112 in turn also has a transport device 120 for transporting an analytic test tape (again not illustrated in FIG. 2). Said device in turn comprises an axle structure, which once again has a two-part design in the illustrated exemplary embodiment. However, analogously to FIG. 1, another design is once again also possible. In this two-part axle structure, one axle 122 is once again held in a base plate 124 or in another carrier element. Applied to this axle 122 is a gearwheel axle 126, which once again has a gearwheel 128 at the lower end thereof and/or another type of coupling element for coupling the gearwheel axle 126 to a drive.

The gearwheel axle 126 in turn has a step 132 that holds the take-up reel 118. Like in the exemplary embodiment as per FIG. 1 as well, there however preferably is no direct contact between the step 132 and the take-up reel 118. The take-up reel 118 and the gearwheel axle 126 are once again coupled by friction to one another by means of a friction clutch 110. Here, the friction clutch 110 once again has a first friction element 148 that is connected to the gearwheel axle 126 and/or is part of the gearwheel axle 126 and hence can be connected to the drive, and also a second friction element 150 that is connected or can be connected to the reel, in this case the take-up reel 118.

The second friction element 150 is once again for example embodied in the form of one or more friction sleeves 134, for example once again in the form of two diametrically opposed friction sleeves 134. These can for example once again be connected to the take-up reel 118 via pick-up pins 136 and/or can be a fixed component of the take-up reel 118. Other connections to the take-up reel 118 are also feasible.

In contrast to the embodiment as per FIG. 1, the friction sleeves 134 in the illustrated exemplary embodiment have a conical design and have friction surfaces 154 that are tilted with respect to the axle 122.

For its part, the first friction element 148 preferably has a two-part design in this exemplary embodiment and has a first cone 156 above the friction sleeves 134 and a second cone 158 below the friction sleeves 134. The first and the second cone 156 and 158 can for example in turn be connected to the gearwheel axle 126 via pick-up pins 160 and 162. However, in principle, another embodiment is also possible, for example integration or a fixed connection between the cones 156, 158 and the gearwheel axle 126.

For their part, the cones 156, 158 provide friction surfaces that are tilted with respect to the axle 122, namely a first conical surface 164 and a second conical surface 166, which interact with the titled friction surfaces 154 of the friction sleeves 134. Once again there is an entrainment effect between the first friction element 148 and the second friction element 150 up to a limit torque or a limit torque range in which static friction acts, whereas the first friction element 158 slips over the second friction element 150 if this limit torque is exceeded.

Once again, provision can be made for the contact force, by means of which the first friction element 148 is pressed onto the second friction element 150 and/or vice versa, to be adjustable. To this end, an adjustment nut 138 has once again been provided in the illustrated exemplary embodiment and it is for example in turn screwed onto the gearwheel axle 126 by means of a fine thread. Provision can in turn also be made for a lock nut 140 for securing the adjustment nut.

By way of example, the adjustment nut 138 can act directly on the first cone 156 in the illustrated exemplary embodiment. However, a design is illustrated in which the adjustment nut 138 acts on the first cone 156 via a spring element 168. The can ensure a mechanically robust design. By way of example, the first cone 156 may be provided with enlarged bores for the pick-up pins 160 such that the pick-up pins 160 have a certain amount of play in these bores, and so the spring element 168 can bring about a small change in the position of the first cone 156 in the axial direction.

By way of example, all friction surfaces are once again also provided with the same material pairings in the illustrated exemplary embodiment as per FIG. 2. Thus, for example, the first cone 156 and the second cone 158 can be produced from identical material, and so there are the same material pairings or friction pairings at a transition between the first cone 156 and the friction sleeves 134 and at the transition between the second cone 158 and the friction sleeves 134. However, once again, another embodiment is also possible, i.e. an embodiment with different material pairings.

In the second exemplary embodiment as per FIG. 2, the torque is transmitted to the take-up reel 118 by means of the conical surfaces 164, 166. In the process, the gearwheel 128 on the gearwheel axle 126 is rotated and hence acts indirectly on these conical surfaces 164, 166. These are in turn preferably arranged such that no further friction surfaces influence the torque to be transmitted. The pretension of the cones 156, 158 between gearwheel 128 and friction sleeves 134 is set by the adjustment nut 138, which presses against the spring element 168, e.g. a spiral spring. To this end, use is once again preferably made of a fine thread for allowing a finer adjustment by means of the adjustment nut 138. It is once again feasible that, during series production and when taking into account tolerances, another type of connection, e.g. a snap-on connection, is implemented instead of an adjustment nut; this would once again be easier to assemble and cheaper.

In the illustrated example, a contact force between the first friction element 148 and the second friction element 150 does not act only in the axial direction, but perpendicular to the conical surfaces 164, 166 with a radial component.

Like the illustration in FIG. 1 as well, the illustration of the second exemplary embodiment in FIG. 2 should also merely be understood as an illustration of the principle. Further embodiment options, e.g. developments of the embodiment illustrated in FIG. 2, are also feasible within the scope of the present invention. Once again, the illustrated friction clutch 110 can in an ideal case also be wholly integrated into the tape magazine 114, for example into the take-up reel 118. However, an embodiment completely lacking the tape magazine 114 is also feasible, for example an embodiment in which the analysis tape is introduced into the analytic test instrument 112 without the use of a tape magazine, for example only by means of one or more reels and/or as an individual analysis tape. In respect of the drive of the analytic test instrument 112, i.e. components that are not illustrated in FIG. 2, reference can once again be made in an exemplary fashion to WO 2008/138443 A1 or WO 2009/037341 A1 or the exemplary embodiment as per FIG. 3. By way of example, provision can be made for an automatic drive, for example by means of an electric motor and/or a manual operation, for example by means of a manually actuatable actuator. Various embodiments of a specific type are feasible.

Figure 3:
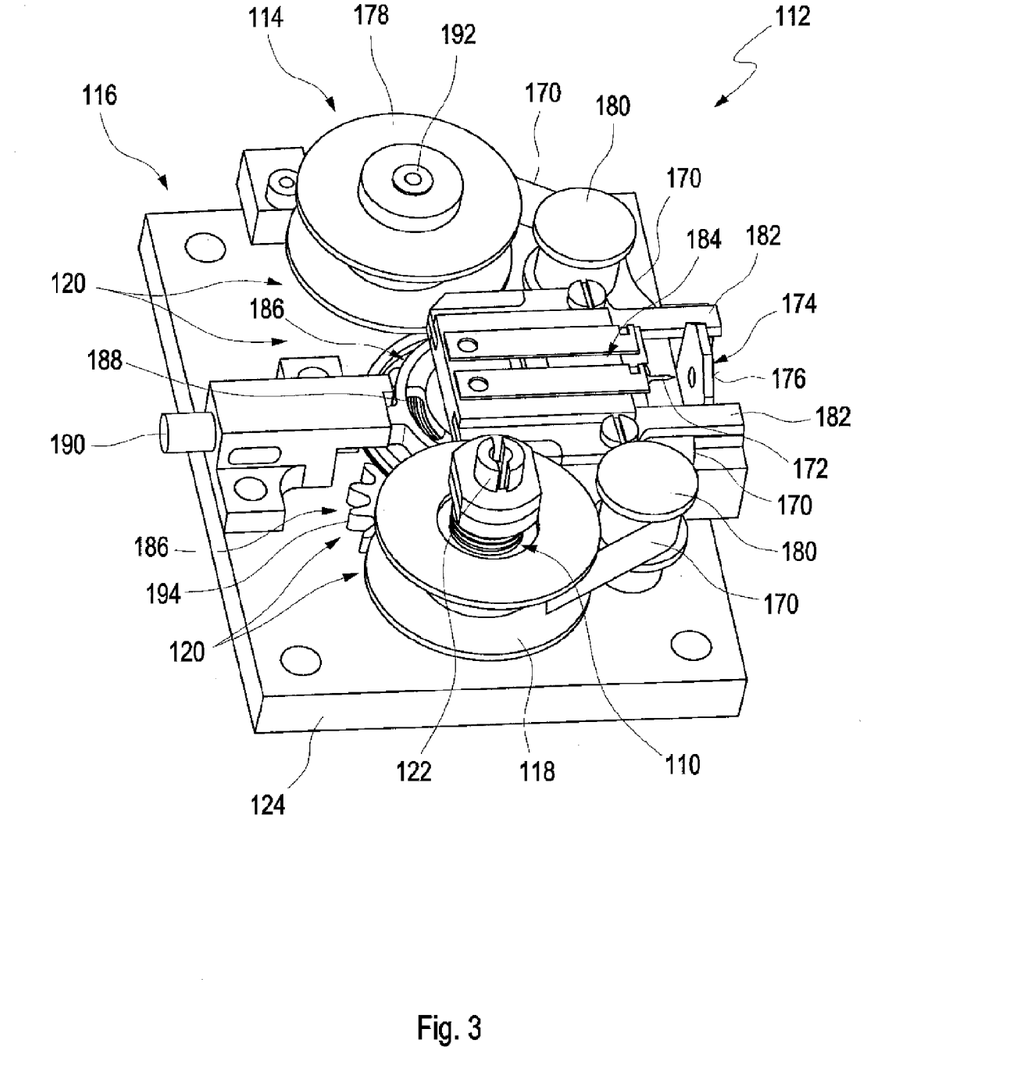
FIG. 3 shows an exemplary embodiment of an analytic test instrument.

FIG. 3 illustrates, in a very schematic perspective illustration, an exemplary embodiment of an analytic test instrument 112. The analytic test instrument 112 comprises an analysis tape 170, which is transported in the analytic test instrument 112 by means of a transport device 120. By way of example, the analysis tape 170 may comprise a plurality of analytic aids 172, which are arranged, for example, one behind the other in a direction of the tape, on the analysis tape 170 or a carrier tape of the analysis tape 170 and can for example be used in succession in an application position 174 of the analytic test instrument 112. By way of example, provision can be made for a contact surface 176 in this application position 174 for resting against a skin surface of a user. Only one analytic aid 172 is indicated in FIG. 3.

The transport device 120 comprises a supply reel 178, on which sections of the analysis tape 170 with yet to be used analytic aids 172 are held, and a take-up reel 118, on which sections of the analysis tape 170 with used analytic aids 172, e.g. lancets, are held. By way of example, the analysis tape 170 can be routed to the application position 174 by means of deflectors 180, in particular deflection rollers. By way of example, in the illustration as per FIG. 3, the supply reel 178 and the take-up reel 118 rotate clockwise. Before the analysis tape 170 reaches the application position 174, it can be routed through a tape guide 182, for example such that the analytic aids 172 are deflected from a vertical plane into a horizontal plane, for example parallel to a basic plate 124. Such a deflection can be dispensed with in the case of other types of analytic aids 172, e.g. test elements.

In the application position 174, the analytic aids 172 are for example gripped by a gripper 184 or gripper system and used as intended. By way of example, a sample-taking motion and/or a lancet motion can be carried out. In the latter case, a lancet can for example pass through an opening in the contact surface 176 and perforate skin of a user. The movement of the gripper 184 or gripper system can for example take place on a carriage and can for example be driven by a drive, illustrated here by a drive unit 186. The drive unit 186 is merely indicated in FIG. 3 and can for example be embodied like the drive mechanisms illustrated in WO 2008/138443 A1 or WO 2009/037341 A1. By way of example, the drive unit 186 may comprise a spring element 188 and/or another type of energy store. By way of example, it may comprise this spring element 188, a spiral spring, which drives a wheel of the drive unit 186 to perform rotational motion, as a result of which e.g. the gripper 184 is driven, in particular in a linear motion in the direction of the contact surface 176. In particular, the drive unit 186 can be triggered by a trigger 190, for example a trigger 190 that releases the wheel of the drive unit 186.

The supply reel 178 and the take-up reel 118 can each be mounted on axles 192 and 122. The transport device 120 or the drive 186 thereof can for example comprise a gearwheel 194 that can for example likewise be driven by the spring element 188 and/or another part of the drive unit 186 and that for example can interact with a gearwheel 128 (not visible in FIG. 3) of the axle 122 of the take-up reel 118 in order to drive said axle.

In the illustrated exemplary embodiment, the axle 122 of the take-up reel 118 comprises a friction clutch 110. By way of example, this friction clutch 110 can be embodied analogously to the exemplary embodiment illustrated in FIG. 2. However, in principle, other embodiments are also possible. The friction clutch 110 offers the aforementioned advantages and for example compensates changes in the torque as a result of a reliably changing degree of winding on the take-up reel 118 and for example prevents damage to the analysis tape 170 and/or the gripper 184.

Reference is made to the fact that the analytic test instrument 112 in FIG. 3 has been shown in a very schematic fashion. A possible housing has not been illustrated. Nor has a separation between a basic instrument 116 and a tape magazine 114, which may optionally be present, been illustrated. Numerous other embodiments of the analytic test instrument 112 using one or more friction clutches 110 are possible.

Figure 4:
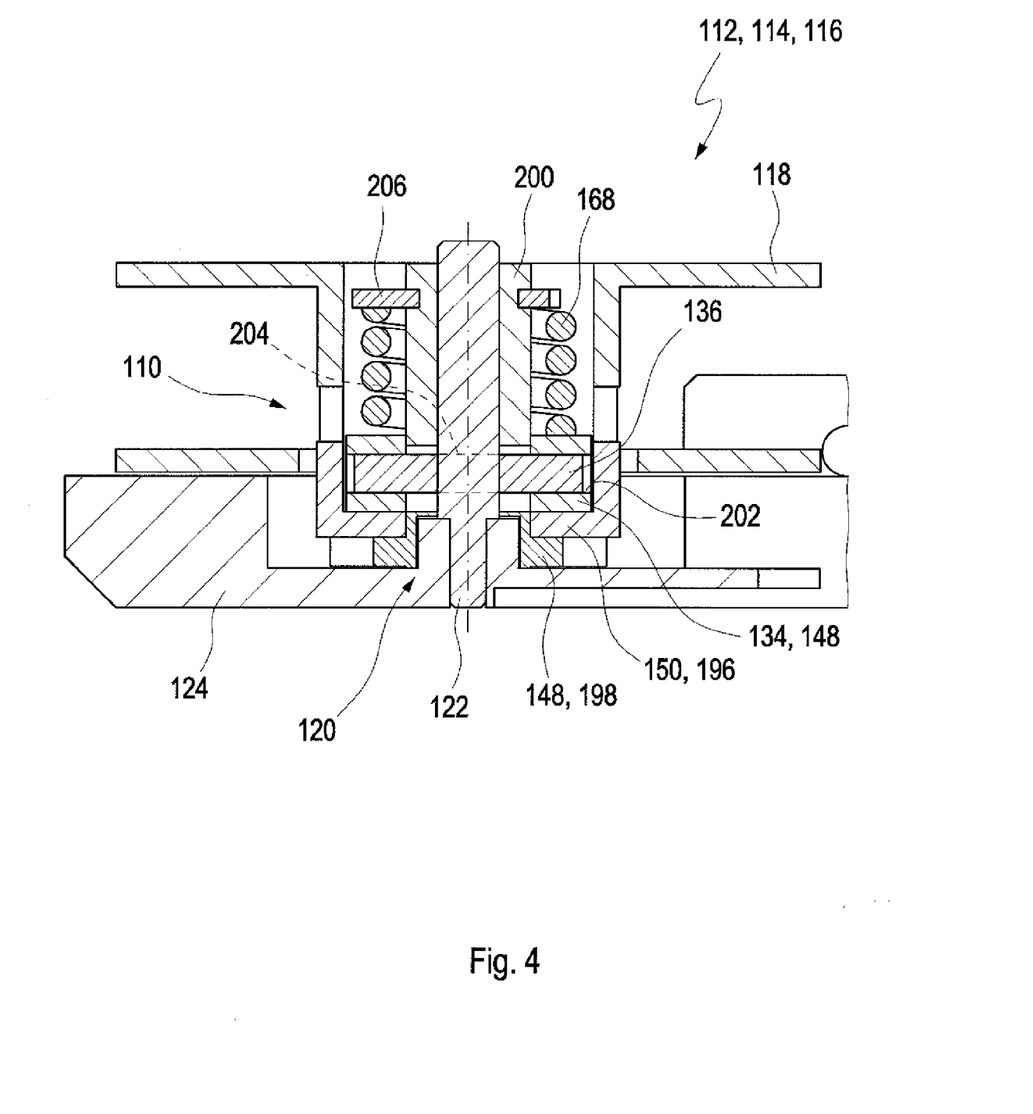
FIG. 4 shows a third exemplary embodiment of a friction clutch for an analytic test instrument.

FIG. 4 illustrates a further exemplary embodiment of an analytic test instrument 112 according to the invention with a friction clutch 110. The exemplary embodiment corresponds in large parts to the exemplary embodiment as per FIG. 1, and so reference can largely be made to this figure. Once again, a take-up reel is preferably entrained in this exemplary embodiment on the basis of purely axial frictional forces, i.e. ones acting parallel to the axle, between a first friction element 148 and a second friction element 150. However, in principle, a slight tilt of the frictional forces relative to the axle 122 is also possible, preferably a tilt of no more than 10 degrees.

In the illustrated exemplary embodiment, the first friction element 148 once again has a two-part design, similar to the exemplary embodiment as per FIG. 1. Here, the second friction element 150, which is connected to the take-up reel 118, is embodied as a disk-shaped extension 196, which extends inward from the actual take-up reel 118, toward the axle 122, and which can be connected to the rest of the take-up reel 118 as one piece or else in the form of a disposable connection or a detachable connection. This disk-shaped extension 196 is embedded between an upper part of the first friction element 148, which is embodied as a friction sleeve 134 in this case, and a lower part of the first friction element 148, which in this case is embodied as an outwardly projecting step 198 of the body 200 of the friction clutch 110 that has been applied to the axle 122 or is fixedly connected to the axle 122. Thus, contrary to the exemplary embodiment as per FIG. 1, the friction sleeve 134 is not part of the second friction element 150 in this exemplary, but rather part of the first friction element 148. A mixed form is also feasible, embodiment one or more friction sleeves 134 associated with the first friction element and having one or more friction sleeves 134 associated with the second friction element 150. In the exemplary embodiment illustrated in FIG. 4, the friction sleeve 134 is embodied as a cylinder ring, with an internal diameter embodied such that the cylinder ring can be pushed over the body 200 of the friction clutch 110, preferably precisely or with play of no more than a few tenths of a millimeter. In the radial direction, one, two or more bores 202 are accommodated in the cylinder ring of the friction sleeve 134, through which bores the pick-up pins 136 or the pick-up pin 136 extend. In the exemplary embodiment illustrated in FIG. 4, the pick-up pin 136 in turn is, for its part, embodied as a single pick-up pin 136 in an exemplary fashion, which extends through a further bore 204 in the axle 122. This bore 204 is preferably embodied as a slot bore and has a dimension in the axial direction that exceeds the diameter of the pick-up pin 136. However, the dimension of the bore 204 perpendicular to the axle is preferably matched to the dimension of the pick-up pin 136. Accordingly, the pick-up pin 136 has play in the axial direction, whereas there preferably is no play perpendicular to the axle.

The friction sleeve 134 is accordingly mounted on the body 200 of the friction clutch 110 such that it can move in the axial direction. Once again, provision is made for a spring element 168, which in this case exerts spring force on the friction sleeve 134, directed downward, i.e. toward the disk-shaped extension 196, in FIG. 4. At the opposite end thereof, the spring element 168 is counter-borne, for example, as illustrated in FIG. 4, by means of a securing ring 206. In the illustrated exemplary embodiment, the spring element 168 is embodied as a spiral spring. Other embodiments of the spring element 168 and the counterbearing are also feasible. The spring element 168 presses the friction sleeve 134 against the disk-shaped extension 196, and so a frictional force is generated between this disk-shaped extension 196 and the friction sleeve 134 and the step 198. The take-up reel 118 is accordingly entrained when the axle 122 is rotated, provided a counter-torque does not exceed the pick-up torque exerted by the friction between the friction elements 148, 150.

Developments of the embodiment illustrated in FIG. 4 are also possible. Thus, the step 198 of the first friction element 148 may also be replaced by another type of projection, which need not necessarily be fixedly connected to the body 200. Thus, instead of an integral embodiment of the step 198 and the body 200, use can for example also be made of a detachable connection or a singly producible connection between a projection and the body 200. Furthermore, the design shown in FIG. 4 can also be reversed, and so, for example, the friction sleeve 134 can also be embodied as lower part of the first friction element 148 and the step 198 can be embodied as upper part of the first friction element 148. Furthermore, the spring element 168 can also for example be complemented and/or replaced by means of an adjustment element, for example analogously to the embodiment in FIG. 1. By way of example, this can also be brought about by means of a friction sleeve 134 that can be displaced onto the body 200 in the axial direction, analogously to the embodiment in FIG. 4. Accordingly, the embodiments in FIGS. 1 and 4 may also be combined.

In the exemplary embodiment illustrated in FIG. 4, the first friction element 148 has a two-part or, in general, a multipart design (wherein provision can also be made for more than two parts). However, this is not necessarily the case. Alternatively, or in addition thereto, the second friction element 150 can also have a two-part or multipart design, and so, for example, the latter can have at least two parts, between which at least one part of the first friction element 148 is arranged. Various embodiments are feasible.

| List of reference signs | |
|---|---|
| 110 | Friction clutch |
| 112 | Analytic test instrument |
| 114 | Tape magazine |
| 116 | Basic instrument |
| 118 | Take-up reel |
| 120 | Transport device |
| 122 | Axle |
| 124 | Basic plate |
| 126 | Gearwheel axle |
| 128 | Gearwheel |
| 130 | Securing nut |
| 132 | Step |
| 134 | Friction sleeve |
| 136 | Pick-up pins |
| 138 | Adjustment nut |
| 140 | Lock nut |
| 142 | Underside |
| 144 | First O-Ring |
| 146 | Second O-Ring |
| 148 | First friction element |
| 150 | Second friction element |
| 152 | Intermediate elements |
| 154 | Tilted friction surface |
| 156 | First cone |
| 158 | Second cone |
| 160 | Pick-up pins |
| 162 | Pick-up pins |
| 164 | First conical surface |
| 166 | Second conical surface |
| 168 | Spring element |
| 170 | Analysis tape |
| 172 | Analytic aid |
| 174 | Application position |
| 176 | Contact surface |

-continued

| List of reference signs | |
|---|---|
| 178 | Supply reel |
| 180 | Deflector |
| 182 | Tape guide |
| 184 | Gripper |
| 186 | Drive unit |
| 188 | Spring element |
| 190 | Trigger |
| 192 | Axle |
| 194 | Gearwheel |
| 196 | Disk-shaped extension |
| 198 | Step |
| 200 | Body |
| 202 | Bore |
| 204 | Bore |
| 206 | Securing ring |

The invention claimed is:

1. An analytic test instrument, having at least one transport device for an analysis tape, wherein the analysis tape comprises a plurality of analytic aids that are used in succession, wherein the transport device comprises at least one friction clutch, wherein the friction clutch has at least one first friction element coupled to a drive and at least one second friction element coupled to a reel of the analysis tape, wherein the first friction element and the second friction element are coupled by friction such that the first friction element entrains the second friction element in a first torque range and slips over the second friction element in a second torque range, wherein at least one intermediate element is sandwiched between the first friction element and the second friction element, wherein the first friction element and the second friction element are adjacent to one another, wherein the intermediate element has elastic properties, wherein the second friction element is embedded between two first friction elements in the axial direction, wherein at least one axial force component acts on the second friction element, the analytic test instrument further comprising:
an axle extending in the axial direction; and
wherein the first friction element and the second friction element are arranged in the axial direction along the axle.

2. The analytic test instrument as claimed in claim 1, wherein a transition between the first torque range and the second torque range is predetermined by a transition between static friction and dynamic friction between the first friction element and the second friction element.

3. The analytic test instrument as claimed in claim 1, wherein the friction clutch is arranged between an axle and an element surrounding the axle, in particular a reel of the analysis tape.

4. The analytic test instrument as claimed in claim 1, wherein at least one of the friction elements comprises at least one friction sleeve.

5. The analytic test instrument as claimed in claim 4, wherein the friction sleeve comprises at least one friction surface that is tilted with respect to the axle, wherein the first friction element comprises at least one conical friction surface arranged in a concentric fashion to the axle, which conical friction surface interacts, coupled by friction, with the tilted friction surface.

6. The analytic test instrument according to claim 5, wherein the conical friction surface comprises a first conical surface arranged on a first side of the friction sleeve and a second conical surface arranged on an opposite side of the friction sleeve.

7. The analytic test instrument as claimed in claim 1, wherein the first friction element and/or the second friction element comprises at least one conical friction surface.

8. The analytic test instrument as claimed in claim 1, wherein the friction coupling between the first friction element and the second friction element is brought about via the at least one intermediate element, in particular at least one O-ring.

9. The analytic test instrument as claimed in claim 1, wherein provision is made for at least one adjustment element, wherein the adjustment element makes it possible to adjust a frictional force between the first friction element and the second friction element.

10. The analytic test instrument as claimed in claim 9, wherein the adjustment element comprises at least one adjustment nut.

11. The analytic test instrument as claimed in claim 1, wherein provision is made for at least one spring element, wherein the spring element is designed to influence a frictional force between the first friction element and the second friction element.

12. The analytic test instrument as claimed in claim 1, wherein the same material pairs are present at each point of contact between the first friction element and the second friction element.

* * * * *